US00PP22949P3

(12) United States Plant Patent
Buck et al.

(10) Patent No.: US PP22,949 P3
(45) Date of Patent: Aug. 14, 2012

(54) APPLE TREE NAMED 'PREMIER STAR'

(50) Latin Name: *Malus pumila Mil*
Varietal Denomination: Premier Star

(75) Inventors: Stephanie Buck, Hope (NZ); Arthur G. Buck, Hope (NZ)

(73) Assignee: Premier Star Limited (NZ)

( * ) Notice: Subject to any disclaimer, the term of this patent is extended or adjusted under 35 U.S.C. 154(b) by 0 days.

(21) Appl. No.: 12/807,537

(22) Filed: Sep. 7, 2010

(65) Prior Publication Data

US 2012/0060246 P1 Mar. 8, 2012

(51) Int. Cl.
*A01H 5/00* (2006.01)

(52) U.S. Cl. ..... Plt./162
(58) Field of Classification Search ..... Plt./162
See application file for complete search history.

(56) References Cited

OTHER PUBLICATIONS

GTITM UPOVROM Citation for 'Premier Star' as per NZ PBR APP155; Sep. 26, 2002.*

* cited by examiner

*Primary Examiner* — Kent L Bell
(74) *Attorney, Agent, or Firm* — Paine Hamblen LLP

(57) ABSTRACT

A new and distinct variety of apple tree is described and which is denominated varietally as 'Premier Star' and which is mature for harvesting and shipment during the month of February under the ecological conditions prevailing near Hope, Nelson, New Zealand.

4 Drawing Sheets

BACKGROUND OF THE NEW VARIETY

The present invention relates to a new and distinct variety of apple tree, *Malus pumila Mil* nd which has been denominated varietally as 'Premier Star'; and more specifically to an apple tree which is principally characterized as to novel by producing an attractive, highly colored apple which is mature for harvesting and shipment at its orchard of origin which is located near Hope, Nelson, New Zealand during the month of February.

ORIGIN AND ASEXUAL REPRODUCTION

It has long been recognized that a very important factor contributing to the success of any variety of apple tree bearing fruit for the fresh markets is its ability to produce an attractively colored fruit which has a distinctive, noteworthy flavor, and which further has good handling and storage characteristics. The new variety 'Premier Star' is noteworthy as producing an attractively and distinctly colored fruit having a bright red blush and which is further ripe for harvesting, processing and/or shipment in Hope, Nelson, New Zealand during the month of February. The present variety of fruit is harvested during the same season with other well known varieties such as the 'Imperial Gala' (unpatented) from which it was derived as a chance mutation; the 'Galaxy' apple tree, U.S. Plant Pat. No. 6,955; the 'Baigent' apple tree, U.S. Plant Pat. No. 10,016; the 'Royal Gala' apple tree, U.S. Plant Pat. No. 4,121; the 'Fulford' apple tree, U.S. Plant Pat. No. 7,598; and the 'Applewaites' apple tree, U.S. Plant Pat. No. 8,720. As noted above, the 'Premier Star' apple tree, of the present invention, was discovered as a chance, branch mutation of an 'Imperial Gala' (unpatented) apple tree that was then growing within the cultivated area of an orchard of the inventors' which is located in Hope, Nelson, New Zealand in 1999. The inventors noted the unique characteristics of the present tree, and marked the chance, branch mutation, for further observation. After observing the chance mutation for several years, and evaluating the fruit produced by same, the inventors removed bud wood from the chance mutation and then asexually propagated it by budding it onto 'M-9' rootstock (unpatented). The newly created trees were then planted in the orchard of origin which is located near Hope, Nelson, New Zealand. Since that time, these first asexually reproduced trees have been continually observed, and have subsequently produced fruit. Further studies of these first asexually produced trees have convinced the inventors that he first asexual propagation of this new variety produced trees which are true to the original chance mutation.

As compared to other apple varieties, that it is most closely similar to, the present variety 'Premier Star' is distinguishable from its parent and other known Gala-type varieties by its distinctive coloration. More particularly, the present variety 'Premier Star' has a coloration which is characterized by a bright red blush which covers approximately 70 to 90 percent of the fruit surface. In comparison the parent, 'Imperial Gala' (unpatented), produces fruit having a distinctive orange-red striping which covers about 50 to 70 percent of the fruit surface. Further, the present variety 'Premier Star' is distinguishable from the variety 'Galaxy' (U.S. Plant Pat. No. 6,955) because this previously patented variety produces fruit having a skin color which is 90 to 100 percent a solid cherry red with indistinct dark red overstriping. Moreover, in comparison to the variety 'Baigent' (U.S. Plant Pat. No. 10,016) the fruit produced by this previously patented tree has a coloration which has bold red striping with flecks of brown color. The present new variety is also distinguishable therefrom because of its bright red blush. In comparison to the variety 'Royal Gala' (U.S. Plant Pat. No. 4,121), which produces fruit having a skin color that has 40 to 60 percent orange-red striping, the new variety is clearly distinguishable therefore in view of its bright red blush. Additionally, relative to the previously patented variety 'Fulford' (U.S. Plant Pat. No. 7,598) which produces fruit having only a 50 to 70 percent bright red blush, the present variety is clearly distinguishable by providing a bright red blush which covers between 70 and 90 percent of the fruit surface. Finally, in connection with the variety 'Applewaites' (U.S. Plant Pat. No. 8,720), the present variety is clearly distinguishable because the fruit of the new variety is harvested some 2 to 4 days after this variety.

SUMMARY OF THE NEW VARIETY

The 'Premier Star' apple tree is characterized principally as to novelty by producing an attractive, highly colored fruit which is ripe for harvesting and shipment during the last week of February under the ecological conditions prevailing near Hope, Nelson, New Zealand. The present variety is easily distinguishable from the fruit produced by the 'Imperial Gala' apple tree (unpatented) from which it was derived as a chance mutation by producing a highly colored fruit which has a 70 to 90 percent bright red blush as compared to the 'Imperial Gala' which produces fruit having orange-red fruit having orange-red striping which covers about 50-70 percent of the fruit surface.

BRIEF DESCRIPTION OF THE DRAWINGS

The accompanying drawings are color photographs of the various aspects of the present tree. The colors are nearly as true as is reasonably possible in color representations of this type. Due to chemical development, processing, and printing the leaves and fruit of the present variety may or may not be accurate when compared to the actual specimen. For this reason, future color references should be made to the color plates as provided by The Royal Horticultural Society Colour Chart, London and other general color descriptions as provided for, hereinafter.

NOT A COMMERCIAL WARRANTY

Figure 1:
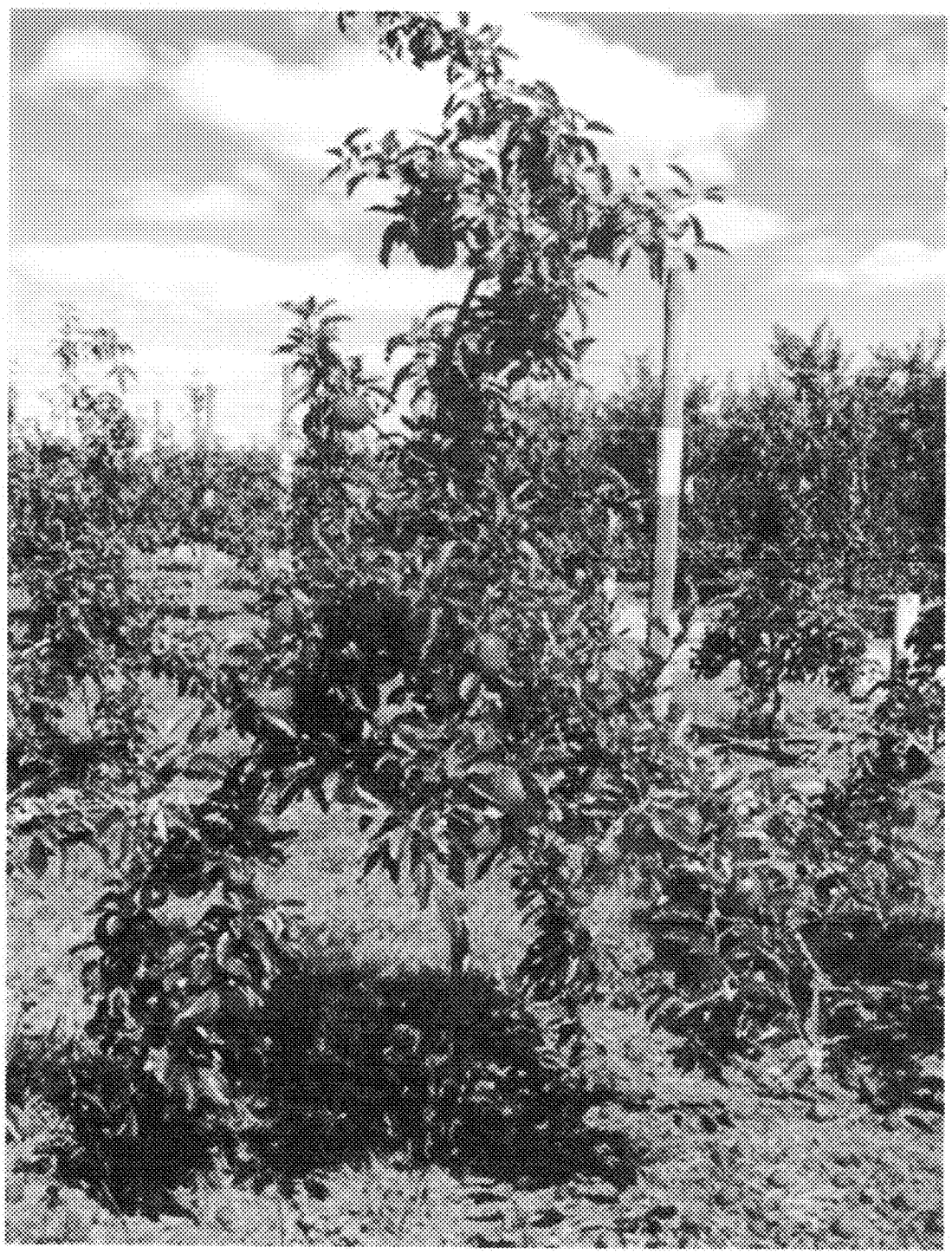
FIG. 1 is a photograph which shows the growth habit of a second generation tree of the variety 'Premier Star' when grown on M-9 rootstock (unpatented) within the orchard of origin which is located near Hope, Nelson, New Zealand.
Figure 2:
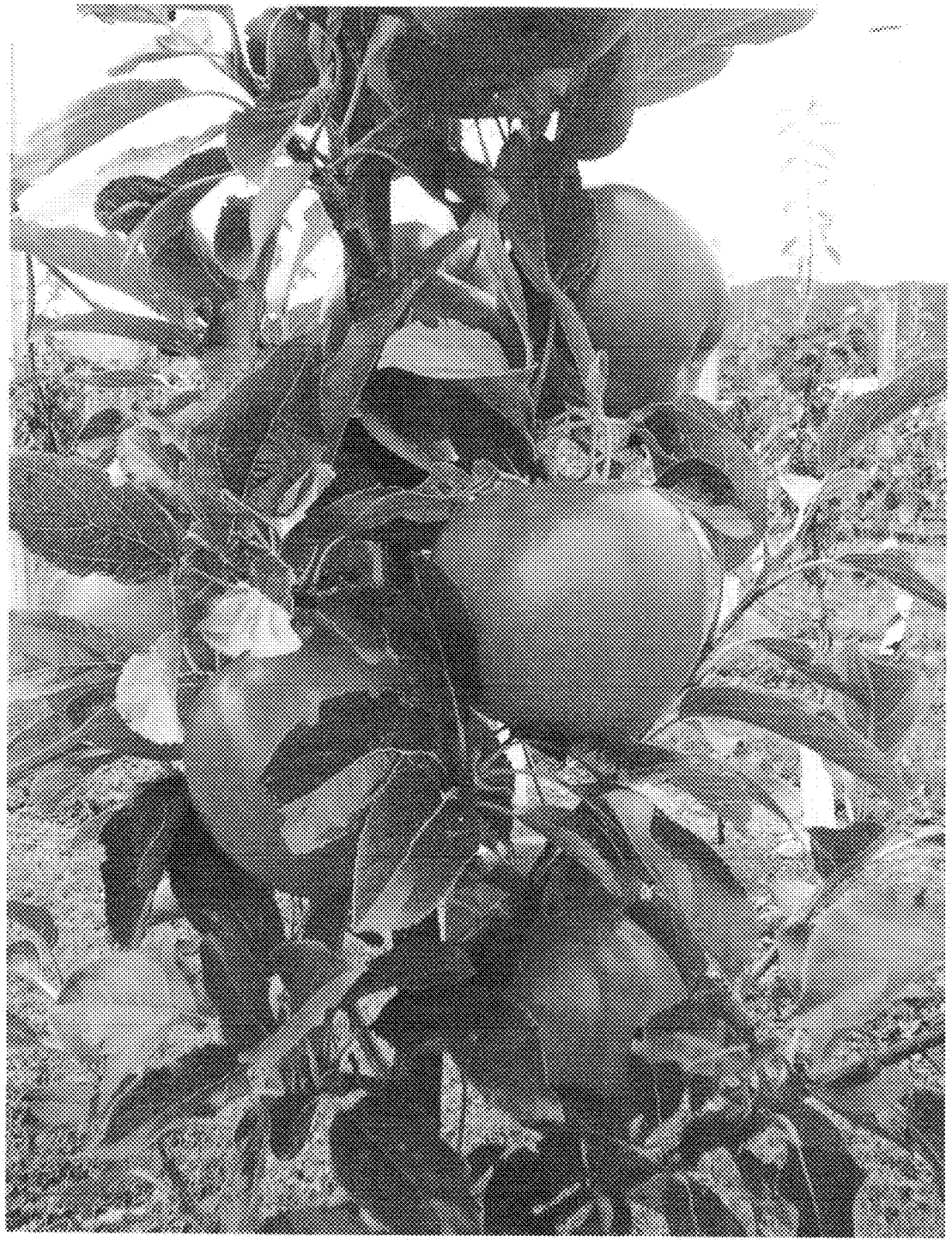
FIG. 2 is a photograph showing the growth habit of the fruit produced by the 'Premier Star' apple tree when grown on the same second generation trees which are grown at the orchard of origin which is located near Hope, Nelson, New Zealand.

The following detailed description has been prepared to solely comply with the provisions of 35 U.S.C. §112, and does not constitute a commercial warranty, (either expressed or implied), that the present variety will, in the future, display the botanical, pomological or other characteristics as set forth, hereinafter. Therefore, this disclosure may not be relied upon to support any future legal claims including, but not limited to, breach of warranty of merchantability, or fitness for any particular purpose, or non-infringement which is directed, in whole, or in part, to the present variety.

DETAILED DESCRIPTION

Referring more specifically to the pomological details of this new and distinct variety of apple tree, the following was observed during the 2009 growing season under the ecological conditions prevailing in a test orchard which is located near Hope, Nelson, New Zealand. All major color code designations are referenced to The Royal Horticultural Society Colour Chart (3$^{rd}$ Edition) provided by The Royal Horticultural Society of Great Britain.

TREE

Size:

*Generally*.—Average as compared to other apple cultivars. The observed, third generation trees, which are 4 years old, are currently growing in an orchard which is located near Hope, Nelson, New Zealand. The observed trees have a height of about 3 meters; and a width or diameter of about 1.2 meters when measured at a height of about 1 meter above the surface of the earth.

Vigor: Considered average for the variety.

Growth type: Ramified.

Growth habit: Spreading.

TRUNK

Size: About 5 cm. in diameter when measured at a location which is about 20 cm. above the graft union.

Bark texture:

*Generally*.—Smooth.

Bark color: Grey-Green (RHS 197D).

Bark lenticels:

*Size*.—About 3.3 mm. long; and about 1.6 mm. wide.

*Color*.—Grey-Yellow (RHS 162D).

*Concentration*.—About 4 bark lenticels are found per square centimeter of bark surface area.

BRANCHES

Size: About 28 mm. in diameter when measured on 2 year old branches at a distance of about 50 cm. from the trunk. The branch length of the present variety is about 300-1200 mm. on 2 year old branches. Further, the intermode length is about 30-200 mm. The present variety's observed branch length, and internode length is similar to the variety 'Imperial Gala' (unpatented) from which it was derived as a chance mutation. Therefore, these characteristics are not distinctive of the present variety.

Crotch angle:

*Generally*.—About 20 degrees below, to about 40 degrees above the horizontal plane. The crotch angle is not distinctive of the present variety, however.

Branches:

*Color*.—Generally speaking, Grey-Brown (RHS 199B).

*Lenticels*.—The present variety produces lenticels which are about 3 mm. long; and about 1 mm. wide.

Branch lenticels:

*Color*.—Grey-Yellow (RHS 162D).

*Concentration*.—About 5 lenticels are found per square meter of bark surface area.

Winter hardiness:

*Generally*.—The present variety is hardy as compared to the region in which it is currently being cultivated, that being, in Hope, Nelson, New Zealand.

Chilling requirements: The present variety appears to have the same chilling requirement as the variety 'Royal Gala' (U.S. Plant Pat. No. 4,121) when grown under the same ecological conditions in Hope, Nelson New Zealand.

Dormant, 1 year old shoots:

*Pubescence*.—Average for the species.

*Size*.—About 40 cm.

*Diameter*.—About 5 mm. The dormant 1 year old shoot length is about 400 mm. The length of 1 year old shoots are indistinguishable from the length of 1 year shoots as seen on the 'Imperial Gala' apple tree (unpatented). Therefore, this characteristic is not distinctive of the present variety.

*Color*.—Grey-Orange (RHS 177B).

*Internode length*.—About 31 mm.

*Lenticels*.—Size — About 1.4 mm. long; and about 1.4 mm. wide.

*Lenticels*.—Density — About 5 lenticels are found per square centimeter.

LEAVES

Leaf position relative to shoot: Considered upwardly dispersed.

Leaf:

*Length*.—Considered average. About 85 mm. when measured on 1 year old shoots.

*Width*.—About 45 mm.

*Overall shape*.—Considered ovate.

*Apex shape*.—Considered acuminate.

*Base shape*.—Considered obtuse.

Leaf marginal form:

*Generally*.—Crenate.

Leaf color:

*Upper surface*.—Dark Green (RHS 139A).

*Lower surface*.—A dull Green (RHS 139C).

Leaf petiole:

*Length*.—About 24.7 mm.

*Diameter*.—About 2 mm.

*Color*.—Green (RHS 138B). The leaf petiole diameter and color is similar to that which is observed on the 'Imperial Gala' apple tree (unpatented) from which the present tree was derived as a chance mutation. Therefore, these plant characteristics do not distinguish the present variety.

Leaf stipules:

*Shape*.—Considered lanceolate.

*Apex*.—Shape — pointed;

*Marginal edge*.—Smooth; Color Green (RHS 138B). The leaf stipule characteristics such as the observed characteristics of the stipule apex; marginal form and color of the stipules is similar to that seen on the variety 'Imperial Gala' (unpatented) from which the present tree was derived as a chance mutation. Therefore, these characteristics are not distinctive of the present variety.

*Length*.—About 8.3 mm. long.

*Width*.—About 2.5 mm.

FLOWERS

Buds:

*Generally*.—One flower bud per spur is normally found.

*Shape*.—Ovoid;

*Apex*.—Pointed;

*Base shape*.—Rounded and smooth. The present apple tree's bud characteristics are indistinguishable from the buds which are seen on the variety 'Imperial Gala' (unpatented). Therefore, these tree characteristics do not distinguish the present variety.

Flower buds:

*Shape*.—Considered pointed.

*Length*.—About 7 mm.

*Diameter*.—About 3 mm.

*Color*.—Grey (RHS 201C).

Flower size at full expansion: About 35 mm. in diameter.

Flowers per cluster: 5 or 6 flowers appear in each cluster.

*Flower height*.—About 18 mm. The flower characteristic of the present variety are indistinguishable from the flowers as seen on the 'Imperial Gala' apple tree (unpatented), and therefore this characteristic is not distinctive of the present variety.

Flower petals:

*Quantity*.—Typically 5 flower petals appear in each flower.

Flower petal orientation:

*Generally*.—Touching.

Flower petal:

*Length*.—About 18 mm.

*Width*.—About 10 mm.

Flower petal apex:

*Shape*.—Rounded.

*Petal shape*.—Ovate;

*Petal apex*.—Rounded;

*Petal base*.—Ovate. The overall petal shape, and form of the base of the petals are indistinguishable from the flower petals as seen on the 'Imperial Gala' apple tree (unpatented), and therefore, is not distinctive of the present variety.

Flower petal margin:

*Form*.—Considered smooth.

Flower petal:

*Upper surface color*.—White (RHS 155D).

Figure 3:
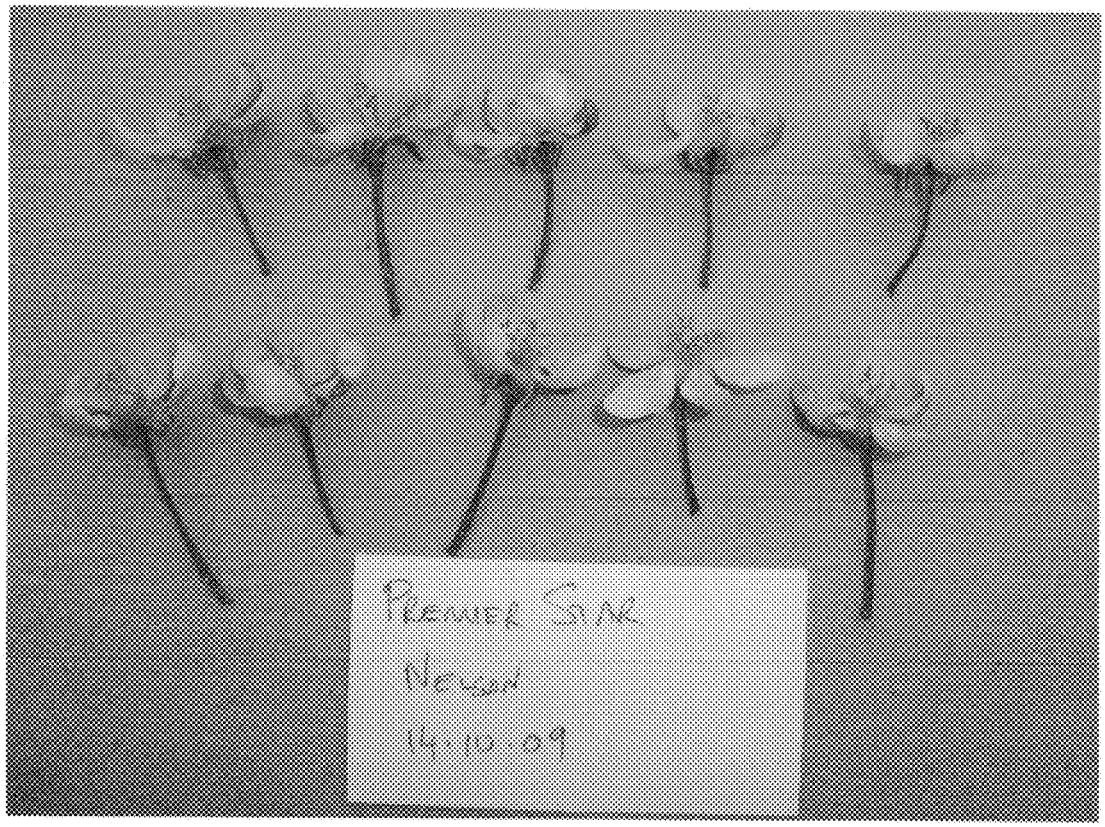
FIG. 3 is a photograph which exhibits the blooming characteristics of second generation 'Premier Star' apple tree now growing on M-9 rootstock (unpatented) at the orchard of origin which is located near Hope, Nelson, New Zealand.
Figure 4:
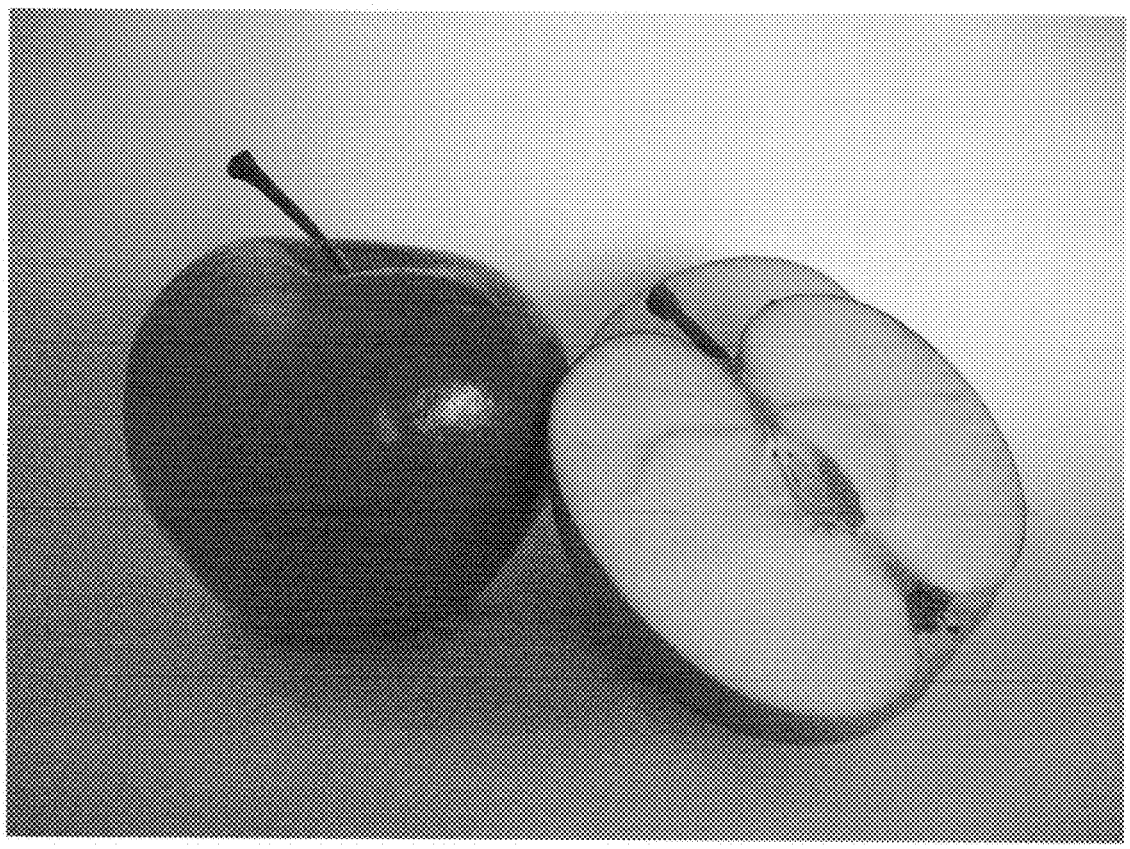
FIG. 4 is a photograph which shows one fruit which is mature for harvesting and shipment and a second fruit divided in the axial plane to show the flesh characteristics thereof.

*Lower surface color*.—Stained with a Reddish-Purple color (RHS 59D) when fully opened. Please see FIG. 3.

Sepals:

*Length*.—About 6 mm.

*Width*.—About 3 mm.

*Color*.—Dorsal surface, Green (RHS 145A).

*Sepal shape*.—Triangular;

*Number of sepals per flower*.—5;

*Apex shape*.—Pointed;

*Marginal form*.—Smooth. The observed sepal shape; numbers; and shape of the sepal apex, and margin are indistinguishable from that seen on the 'Imperial Gala' apple tree (unpatented), and therefore is not considered distinctive of the present variety.

Pedicle:

*Length*.—About 33 mm.

*Pedicel diameter*.—About 2 mm.

*Pedicel color*.—Green RHS 138B). The observed pedicel diameter, and color is similar to that seen on 'Imperial Gala' apple tree (unpatented), and therefore is not considered distinctive of the present variety.

Stamens:

*Quantity*.—Numerous.

Anthers:

*Length*.—About 5 mm.

*Color*.—Yellow (RHS 11C).

Pistil:

*Length*.—About 8 mm. The characteristics of the pistil including its length, number, and color is similar to that seen on the 'Imperial Gala' apple tree (unpatented), and therefore is not considered distinctive of the present variety.

*Color*.—Green (RHS 145C).

Date of full bloom: About 11 Oct. 2009 under the ecological conditions prevailing near Hope, Nelson, New Zealand;

*Blooming period*.—About 2 weeks in Nelson, New Zeland.

Pollination requirement: Similar to that which is required for the 'Royal Gala' apple tree (U.S. Plant Pat. No. 4,121). In this regard, any diploid cultivar (other than 'Royal Gala' or 'Royal Gala' Sports) which flower at similar times can serve to pollinize the new variety 'Premier Star'. The present variety's pollen amount and color, as well as its ovary color, is similar to that which is observed on the 'Imperial Gala' apple tree (unpatented), and is therefore not distinctive of this new variety.

FRUIT

Size: Considered large for the species. Productivity is typically about 80 pounds of fruit per tree for trees grown in high density orchards under the ecological conditions prevailing in Nelson, New Zealand. Inasmuch as productivity and fruit size is greatly influenced by cultural practices, and other ecological factors. These characteristics cannot be considered distinctive of the present variety.

Fruit height: About 66 mm.

Fruit width: About 75 mm.

Fruit shape: Globose and considered conical.

Fruit ribbing: Not present.

*Fruit weight*.—Typically about 6 oz. The fruit weight cannot be considered distinctive of the present variety because it can be influenced by cultural and other ecological factors.

Aperture of the eye:

*Shape*.—Considered closed.

Eye size: Small.

Eye basin:

*Depth*.—About 9 mm.

*Width*.—About 31 mm.

Stalk:

*Size*.—About 2 mm. in diameter.

*Length*.—About 26 mm.

*Color*.—Grey-Brown (RHS 199A).

Stalk cavity:

*Depth*.—About 16 mm.

*Width*.—About 29 mm.

Fruit lenticels:

*Size*.—About 1.4 mm. in both its length and width.

*Density*.—About 4 lenticels are found per square centimeter of fruit surface.

Fruit bloom:

*Generally*.—Absent.

Fruit surface texture:

*Greasiness*.—Considered absent.

Ground skin color: Yellow-Green (RHS 149D).

*Fruit skin thickness*.—Considered average for the species;

*Fruit skin firmness*.—Considered average for the species. The fruit skin thickness and firmness is similar to that seen on the fruit produced by the 'Imperial Gala' apple tree (unpatented). It is therefore not distinctive of the present variety.

Skin overcolor: Bright Red (RHS 45A).

*Pattern*.—Considered a solid blush.

Overcolor:

*Amount*.—Considered high for the species, that is, it is about 70 to 90 percent of the fruit surface.

Amount of russet:

*Eye basin*.—Considered absent, or very low.

*Cheeks*.—Considered absent, or very low.

*Stalk cavity*.—Considered absent, or very low.

Flesh:

*Texture*.—Considered medium, firm and crisp.

*Fruit aroma*.—Weak;

*Fruit flavor*.—Sweet and having mild acidity;

*Eating quality*.—Considered excellent. The fruit flesh aroma, flavor, and eating quality of the flesh is similar to the fruit produced by the 'Imperial Gala' apple tree, and is therefore not distinctive of the present variety.

*Color*.—Considered White (RHS 4D).

Flesh pressure:

*Generally*.—About 7 kilograms to 9 kilograms.

Fruit brix: About 12 degrees to about 13 degrees at the time of harvesting.

*Fruit core symmetry*.—Symmetrical;

*Vascular bundles*.—Small and undefined and not easily discernable to the unaided eye, and therefore not readily measurable. The fruit core characteristics including its symmetry, number of bundles, and it's dimensions, are similar to the unpatented variety 'Imperial Gala', and is therefore not distinctive of the present variety.

SEEDS

Quantity: Typically 5 are found per fruit.

Seeds:

*Color*.—Grey-Orange (RHS 166A).

*Length*.—About 9 mm.

*Width*.—About 6 mm.

Seed locules:

*Numbers*.—5.

*Width*.—About 10 mm.

*Depth*.—About 5 mm.

*Length*.—About 15 mm.

Fruit maturity for consumption: During the months of February and March at Hope, Nelson, New Zealand, the present variety is typically ripe for harvesting and shipment at about February 27, under typical environmental conditions. The date of harvest of this variety typically extends between February 27-March 19.

Fruit use: Primarily for fresh eating for both local and long distance markets, as well as for processed consumption.

Keeping quality: Similar to that of the fruit produced by the 'Royal Gala' apple tree (U.S. Plant Pat. No. 4,121), that is, about 7 days at 60 degrees F.

Resistance to disease and pests: The present variety is considered susceptible to all insects and diseases found in the region of Hope, Nelson, New Zealand. Otherwise, the variety is not known to have any other resistances to diseases common to apple trees.

Although the new variety of apple tree possesses the described characteristics when grown under the ecological conditions prevailing near Hope, Nelson, New Zealand, it should be understood that variations of the usual magnitude and characteristics incident to changes in growing conditions, fertilization, pruning, pest control and horticultural management practices are to be expected.

Having thus described and illustrated our new variety of apple tree, what we claim is new, and desire to secure by Plant Letters Patent is:

1. A new and substantially distinct variety of apple tree, as illustrated and described, and which is characterized as to novelty by bearing an attractively colored apple which is mature for harvesting and shipment during the month of February under the ecological conditions prevailing near Hope, Nelson, New Zealand.

* * * * *

UNITED STATES PATENT AND TRADEMARK OFFICE

CERTIFICATE OF CORRECTION

PATENT NO. : PP22,949 P3
APPLICATION NO. : 12/807537
DATED : August 14, 2012
INVENTOR(S) : Stephanie Buck et al.

It is certified that error appears in the above-identified patent and that said Letters Patent is hereby corrected as shown below:

Column 1, line 4, replace "*Malus pumila Mil* nd" with --"*Malus pumila Mil* and"--.

Column 2, line 11, replace "inventors that he first asexual" with --inventors that the first asexual--.

Signed and Sealed this
Thirtieth Day of October, 2012

David J. Kappos

David J. Kappos
*Director of the United States Patent and Trademark Office*